(12) United States Patent
Kinoshita et al.

(10) Patent No.: US 8,246,597 B2
(45) Date of Patent: Aug. 21, 2012

(54) PANTS-TYPE WEARING ARTICLE

(75) Inventors: Akiyoshi Kinoshita, Kagawa (JP); Natsuko Aoyagi, Kagawa (JP); Kayoko Tanaka, Kagawa (JP); Yasuhiko Kenmochi, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 12/992,334

(22) PCT Filed: Apr. 20, 2009

(86) PCT No.: PCT/JP2009/057825
§ 371 (c)(1),
(2), (4) Date: Nov. 12, 2010

(87) PCT Pub. No.: WO2009/139269
PCT Pub. Date: Nov. 19, 2009

(65) Prior Publication Data
US 2011/0071489 A1 Mar. 24, 2011

(30) Foreign Application Priority Data
May 15, 2008 (JP) ................................. 2008-128916

(51) Int. Cl.
*A61F 13/15* (2006.01)
(52) U.S. Cl. ....... 604/385.29; 604/385.01; 604/385.201; 604/386; 604/389
(58) Field of Classification Search ............. 604/385.24, 604/385.29, 385.01, 385.201, 386, 389, 390, 604/391; 2/912, 913, 914, 915, 919, 96
See application file for complete search history.

(56) References Cited

U.S. PATENT DOCUMENTS

| | | | | |
|---|---|---|---|---|
| 5,108,384 | A * | 4/1992 | Goulait | 604/390 |
| 6,364,863 | B1 * | 4/2002 | Yamamoto et al. | 604/385.27 |
| 6,458,114 | B1 * | 10/2002 | Mishima et al. | 604/385.24 |
| 7,191,497 | B2 * | 3/2007 | Butz | 24/389 |
| 7,640,638 | B2 * | 1/2010 | Kenmochi et al. | 24/442 |
| 2007/0142813 | A1 * | 6/2007 | Sperl | 604/385.31 |
| 2008/0009816 | A1 | 1/2008 | Kenmochi et al. | |
| 2009/0043275 | A1 * | 2/2009 | Perneborn | 604/391 |

FOREIGN PATENT DOCUMENTS
JP     2002-532147 A     10/2002
(Continued)

OTHER PUBLICATIONS
International Search Report from corresponding PCT application No. PCT/JP2009/057825 filed Jul. 21, 2009, 4 pgs.

*Primary Examiner* — Lynne Anderson
*Assistant Examiner* — Bradley Philips
(74) *Attorney, Agent, or Firm* — Brinks Hofer Gilson & Lione

(57) ABSTRACT

A pant-type wearing article configured so as to prevent a lateral zone of a front waist region and an associated lateral zone of a rear waist region which should remain fastened together from being needlessly disengaged from each other. In the pant-type wearing article an outer surface of a base sheet strip constituting a front fastener component is bonded to a fixed region defined on an inner surface of a front lateral zone. The front lateral zone includes a free region to which the base sheet strip is not bonded. The free region normally takes a posture folded back in a waistline direction so that an outer surface of the front lateral zone lies inside.

3 Claims, 7 Drawing Sheets

FOREIGN PATENT DOCUMENTS

| | | |
|---|---|---|
| JP | 2004-505672 A | 2/2004 |
| JP | 2005-533529 A | 11/2005 |
| JP | 2007-504884 A | 3/2007 |
| JP | 2008-012115 | 1/2008 |
| WO | WO 00/35398 A1 | 6/2000 |
| WO | WO 02/11657 A1 | 2/2002 |
| WO | WO 03/057116 A1 | 7/2003 |
| WO | WO 2005/025472 A1 | 3/2005 |
| WO | WO-2005025472 * | 3/2005 |

* cited by examiner

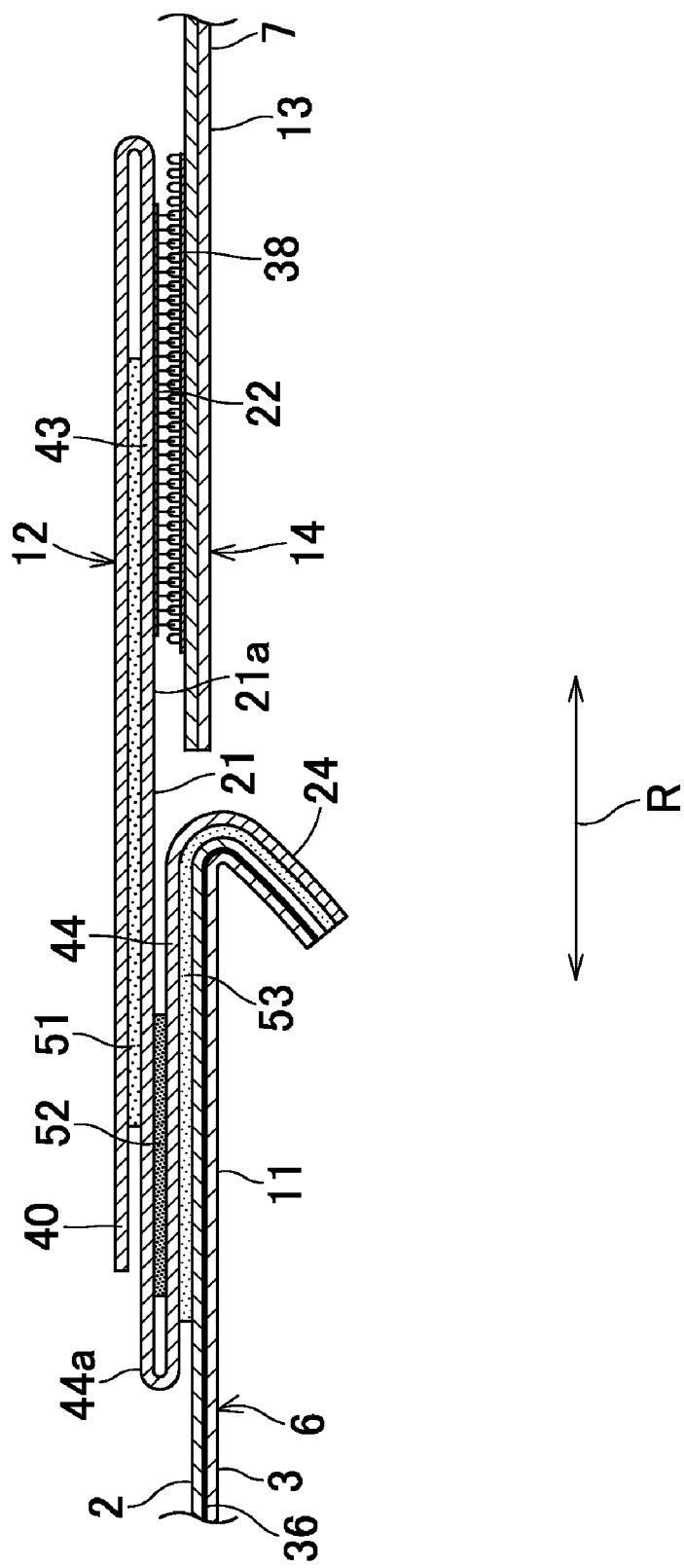

PANTS-TYPE WEARING ARTICLE

RELATED APPLICATION

This application is a 35 U.S.C. §371 national phase filing of International Patent Application No. PCT/JP2009/057825, filed Apr. 20, 2009, through which and to which priority is claimed under 35 U.S.C. §119 to Japanese Patent Application No. 2008-128916, filed May 15, 2008.

TECHNICAL FIELD

The present invention relates to pant-type wearing articles suitable for use in the form of disposable diapers, disposable toilet-training pants or disposable pants.

RELATED ART

In pant-type disposable wearing articles, it is known to connect front and rear waist regions to each other in a detachable manner by a fastener along respective pairs of transverse opposite lateral zones thereof. For example, JP2002-532147 T (PATENT DOCUMENT 1) discloses a training pant in which side flaps of a front waist region are provided on respective outer surfaces with hook-type fastening means and the side flaps of a rear waist region are formed of a nonwoven fabric so that hook-type fastening means may be detachably engaged with the respective outer surfaces of the associated rear waist region's side flaps. The front waist region's side flaps as well as the rear waist region's side flaps fully extend from a periphery of a waist-opening to the peripheries of respective leg-openings as viewed in the vertical direction of the training pant. The hook-type fastening means also extend in this manner. Specifically, the front waist region's side flaps may be placed on respective inner surfaces of the associated rear waist region's side flaps and then the front and rear waist regions' side flaps may be engaged together to connect the front and rear waist regions to each other so as to obtain the training pant.

The JP2008-012115 A (PATENT DOCUMENT 2) discloses a pant-type wearing article in which the front and rear waist regions are detachably connected to each other along respective pairs of lateral zones thereof by a fastener. The fastener comprises hook members attached to an outer surface of the front waist region along respective lateral zones thereof and loop members attached to the inner surface of the rear waist region along the respective lateral zones thereof. Both hook members and the loop members fully extend from the waist-opening to leg-openings as viewed in the vertical direction of the wearing article. The respective inner surfaces of the rear waist region's lateral zones may be placed on the respective outer surfaces of the front waist region's lateral zones and then the front and rear waist regions may be connected by the fastener to obtain the pant-type wearing article.
[PATENT DOCUMENT 1] JP 2002-532147 T
[PATENT DOCUMENT 2] JP 2008-012115 A

DISCLOSURE OF THE INVENTION

Problem to be Solved by the Invention

Certainly these known wearing articles are advantageous in that each of these wearing articles can be put on a baby while standing, defecation or urination can be checked while standing the baby up, and the lateral zones of the wearing article can be easily opened to take the used wearing article off from the baby. However, in the case of the training pant disclosed in PATENT DOCUMENT 1, the side flap of the rear waist region might be needlessly disengaged from the associated side flap of the front waist region when the side flap comes in contact with the hand(s) of a wearer or a garment worn by the wearer depending on the manner of such contact. This anxiety is true also for the wearing article disclosed in PATENT DOCUMENT 2. Specifically, the lateral zone of the rear waist region having the loop members engaged with the hook members provided on the outer surface of the front waist region's lateral zone might begin to be needlessly disengaged from the associated lateral zone of the front waist region when this lateral zone comes in contact with the hand (s) of the wearer or the garment, depending the manner of such contact.

It is an object of the present invention to provide a pants-type wearing article improved so as to prevent the lateral zone of the front waist region and the associated lateral zone of the rear waist region which should remain fastened together from being needlessly disengaged from each other as the known pant-type wearing article have been the case.

Measure to Solve the Problem

According to the present invention, by there is provided an improvement in a pant-type wearing article having a front-rear direction, a vertical direction and a waistline direction and comprising a crotch region, a front waist region extending forward from the crotch region and a rear waist region extending rearward from the crotch region wherein a pair of front lateral zones of the front waist region opposed to each other in the waistline direction and extending in the vertical direction are detachably connected to a pair of rear lateral zones of the rear waist region opposed to each other in the waistline direction and extending in the vertical direction via a pair of fastener systems so as to form a waist-opening and a pair of leg-openings and the fastener systems extend from the waist-opening to the leg-openings.

An improvement according to the present invention is characterized in that each of the fastener systems comprises a first fastener component on a side of the article facing the skin of the wearer and a second fastener component on a side of the article facing a garment worn by the wearer and adapted to be lapped on the first fastener component from outside of the wearing article and to be repetitively engaged with and disengaged from the first fastener component wherein the first fastener component is mounted on one of the front lateral zone and the rear lateral zone and the second fastener is mounted on other lateral zone, the first fastener component comprising a base sheet strip provided on an inner surface of the one of the front and rear lateral zones and including a distal region extending outward from the one of the front and rear lateral zones in the waistline direction and an engagement region adapted to be engaged with an inner surface of the second fastener component, the one of the front and rear lateral zones including a fixed region in which the outer surface of the base sheet strip is partially bonded thereto and a free region lying outside the fixed region as viewed in the waistline direction so as to be left free with respect to the base sheet strip, and the free region normally takes a posture folded back in the waistline direction so that the outer surface of the one of the front and rear lateral zones lie inside.

According to one preferred embodiment of the invention, the wearing article includes waist elastic members extending under tension along the waist-opening, leg elastic members extending under tension along peripheral edges of the leg-openings and intermediate elastic members provided between the waist elastic members and the leg elastic members as viewed in the vertical direction and extending under tension in the waistline direction.

According to another preferred embodiment of the invention, the free region includes at least the waist elastic members and the intermediate elastic members and is kept in the posture folded back in the waistline direction under contraction of the waist elastic members and the intermediate elastic members in the waistline direction.

According to still another preferred embodiment of the invention, the free region takes a posture folded back in the waistline direction along a folding line extending in the vertical direction.

According to yet another preferred embodiment of the invention, the free region includes none of the waist elastic members, the leg elastic members and the intermediate elastic members.

Effect of the Invention

In the wearing article according to the present invention, a pair of the front lateral zones and a pair of the associate rear lateral zones are connected by the fastener systems to pant-shape the wearing article. One of the front lateral zone and the rear lateral zone includes the fixed region in which the outer surface of the base sheet strip constituting the first fastener component is bonded to this lateral zone and the free region in which the outer surface of the base sheet strip is not bonded thereto. The free region normally takes the posture folded back in the waistline direction so that the outer surface of the lateral zone lie inside. Such a unique arrangement effectively prevents the hand(s) of the wearer or the garment from coming in contact with the second fastener component engaged with the first fastener component from outside the wearing article. In this way, the second fastener component can be prevented from needlessly beginning to be disengaged from the first fastener component due to the hand(s) of the wearer or the garment coming in contact therewith until the front lateral zones and the rear lateral zones are completely disengaged from each other.

BRIEF DESCRIPTION OF THE DRAWINGS

FIG. 7 is a sectional view taken along the line VII-VII in FIG. 6.

Figure 1:
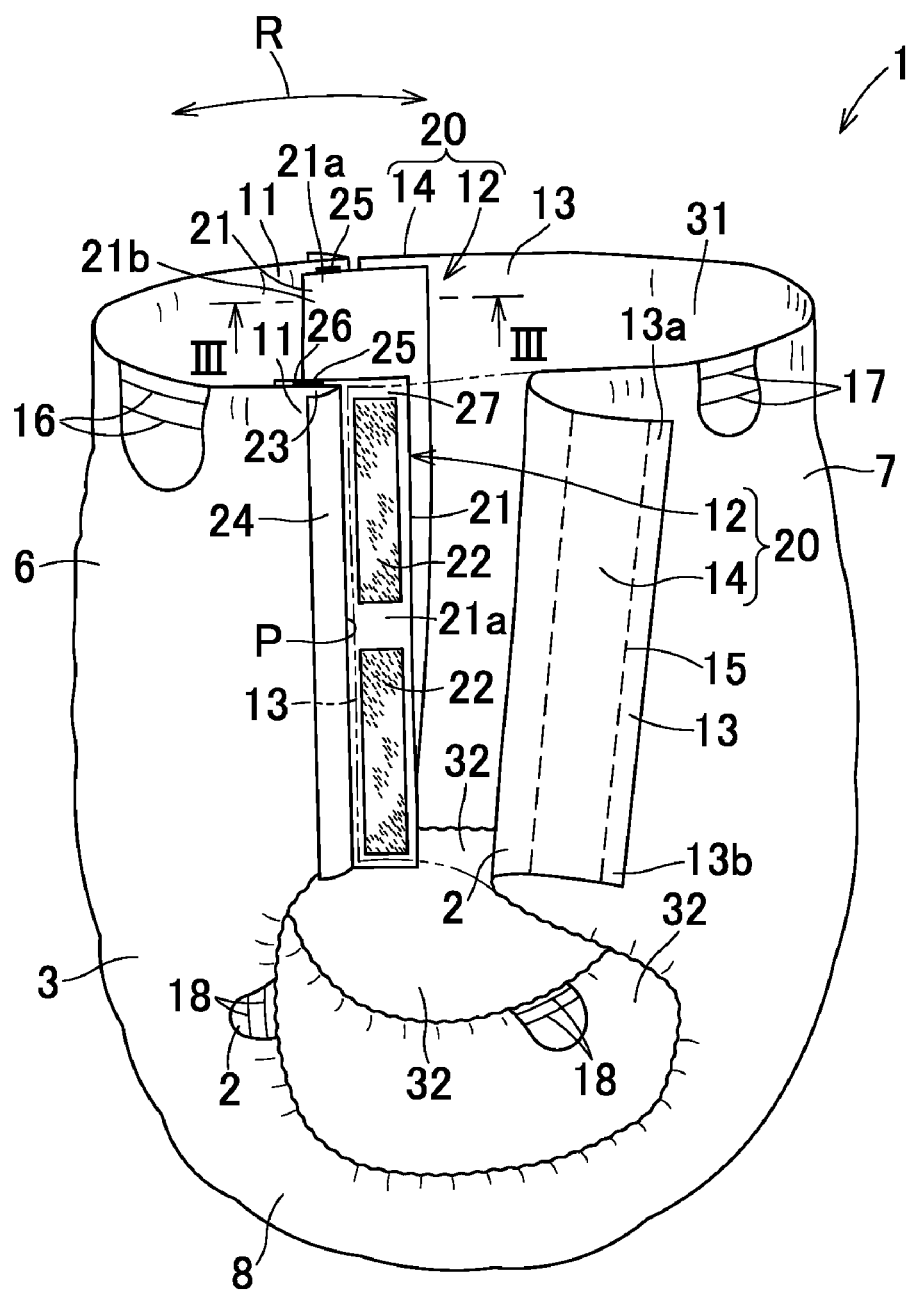
FIG. 1 is a partially cutaway perspective view of a wearing article (disposable diaper) as put on a wearer in pant-like shape.

IDENTIFICATION OF REFERENCE NUMERALS USED IN THE DRAWINGS 1 wearing article (diaper)
6 front waist region
7 rear waist region
8 crotch region
11 front lateral zone
12 front fastener component
13 rear lateral zone
14 rear fastener component
16 waist elastic member
17 leg elastic member
18 leg elastic member
20 fastener system
21 base sheet strip
21a outer surface
22 hook member
23 fixed region
24 free region
31 waist-opening
32 leg-opening
36 elastic member
A front-rear direction
B vertical direction
P folding line
R waistline direction

DETAILED DESCRIPTION OF THE PREFERRED EMBODIMENTS

Details of a pant-type wearing article according to the invention will be more fully understood from the description of a disposable pant-type diaper taken herein as one embodiment thereof given hereunder with reference to the accompanying drawings.

FIG. 1 is a partially cutaway perspective view of a pant-type diaper 1 wherein a front-rear direction, a vertical direction and a waistline direction are indicated by double-headed arrows A, B and R, respectively. The diaper 1 has a front waist region 6, a rear waist region 7 and a crotch region 8 extending between these two regions 6, 7. These regions 6, 7, 8 are defined by a liquid-pervious inner sheet 2 and a liquid-impervious outer sheet 3 lapped over each other and a bodily fluid absorbent core 4 (See FIG. 2) sandwiched between the inner and outer sheets 2, 3. The front waist region 6 has a pair of front lateral zones 11 opposed to each other as viewed in a waistline direction Rand extending in a vertical direction B wherein the respective front lateral zones 11 are formed with front fastener components 12 (See FIG. 2), respectively. In a similar manner, the rear waist region 7 has a pair of rear lateral zones 13 opposed to each other in the waistline direction R and extending in the vertical direction B wherein the respective rear lateral zones 13 are formed with rear fastener components 14. The inner sheet 2 is formed, for example, of a nonwoven fabric and the outer sheet 3 is formed, for example, a plastic film, a nonwoven fabric, or a composite sheet composed of a plastic film and a nonwoven fabric.

The front and rear fastener components 12, 14 cooperate with each other to form a fastener system 20 serving to connect the front and rear waist regions 6, 7 in a detachable fashion. The front fastener component 12 comprises a base sheet strip 21 and a hook member 22 bonded to an outer surface 21a of the base sheet strip 21 so as to constitute a mechanical fastener and to define an engagement region on the outer surface 21a. The base sheet strip 21 lies on the inner surface of the front waist region 6 and formed preferably of a nonwoven fabric, a woven fabric or a plastic film always having stiffness higher than those of the inner sheet 2 and the outer sheet 3. The base sheet strip 21 has an inner surface 21b opposite to the outer surface 21a. The hook component of the mechanical fastener widely known under the trade name of Magic Tape may be used as the hook member 22. The rear fastener component 14 is defined by a portion of the inner sheet 2 in each of the rear lateral zones 13, more specifically, the part defined between a pair of chain lines 15 as illustrated.

This portion of the nonwoven fabric forming the inner sheet 2 operates as a loop member constituting the mechanical fastener adapted to be detachably engaged with the hook member 22. Referring to FIG. 1, one set of front and rear lateral zones 11, 13 on the remote side of FIG. 1 is shown as being connected with each other by the fastener system 20 and the other set of front and rear lateral zones 11, 13 on the near side of FIG. 1 is shown as being disengaged from each other. Dashed double-dotted lines as imaginary lines in FIG. 1 indicate a position occupied by the rear lateral zone 13 when connected with the associated front lateral zone 11.

As will be apparent from FIG. 1, the base sheet strip 21 for the front fastener component 12 has a proximal region 26 bonded to a fixed region 23 of the front lateral zone 11 by an adhesive 25 and a distal region 27 extending outward in the waistline direction R beyond the front lateral zone 11. The distal region 27 is provided with the hook member 22 attached to the outer surface 21a thereof. The front lateral zone 11 includes, in addition to the fixed region 23, a free region 24 extending outward from the fixed region 23 in the waistline direction R and left free with respect to the base sheet strip 21. The free region 24 is folded back in the waistline direction R along a folding line P extending in the vertical direction B with the outer sheet 3 inside.

The diaper 1 is formed with a waist-opening 31 and a pair of leg-openings 32 as the front and rear waist regions 6, 7 are detachably connected together so as to present a pant-like shape. In this state, the front fastener component 12 and the rear fastener component 14 extend from the waist-opening 31 to the leg-openings 32, respectively. It should be appreciated here that, in the case of the front fastener component 12 according to the illustrated embodiment, the base sheet strip 21 extending from the waist-opening 31 to the leg-openings 32 is formed with the hook member 22 divided into upper and lower halves. The front lateral zone 11 of the front waist region 6 extends from the waist-opening 31 to the leg-openings 32 and the free region 24 of the front lateral zone 11 extends along the hook member 22 in the vertical direction B of the diaper 1. Referring to FIG. 1, the rear fastener component 14 provided in the rear lateral zone 13 of the rear waist region 7 which is not yet engaged with the front fastener component 12 as indicated by solid lines is defined by a portion of the inner sheet 2 formed of a nonwoven fabric adapted to serve as the loop member cooperating with the hook member 22. When this nonwoven fabric is lapped upon the hook member 22 from outside as illustrated with imaginary lines and engages with it, the diaper 1 is shaped into a pant adapted to be put on and taken off from the wearer just like the known pant-type diaper. With the diaper 1 in this state, the hand(s) of the wearer or the garment would not come in contact with the rear lateral zone 13 and consequently the rear fastener component 14 would not begin to be needlessly disengaged from the front fastener component 12 so that the rear lateral zone 13 can be prevented from being detached from the front lateral zone 11. This is because the free region 24 of the front waist region 6 lying adjacent the rear lateral zone 13 indicated by the imaginary lines is folded back so as to protrude outward from the diaper 1 and thereby to prevent the hand (s) of the wearer or the garment from coming in contact with the rear lateral zone 13. If upper and/or lower corners 13a, 13b of the rear lateral zone 13 already having been connected to the front lateral zone 11 is or are unintentionally curled off from the front lateral zone 11 due to such contact with the hand (s) of the wearer or the garment, the rear lateral zone 13 may begin to be detached from the front lateral zone 11. However, the free region 24 effectively prevent the hand (s) of the wearer or the garment from coming in contact with the corners 13a, 13b and thereby to prevent the corners 13a, 13b from being curled off from the front lateral zone 11.

Figure 2:
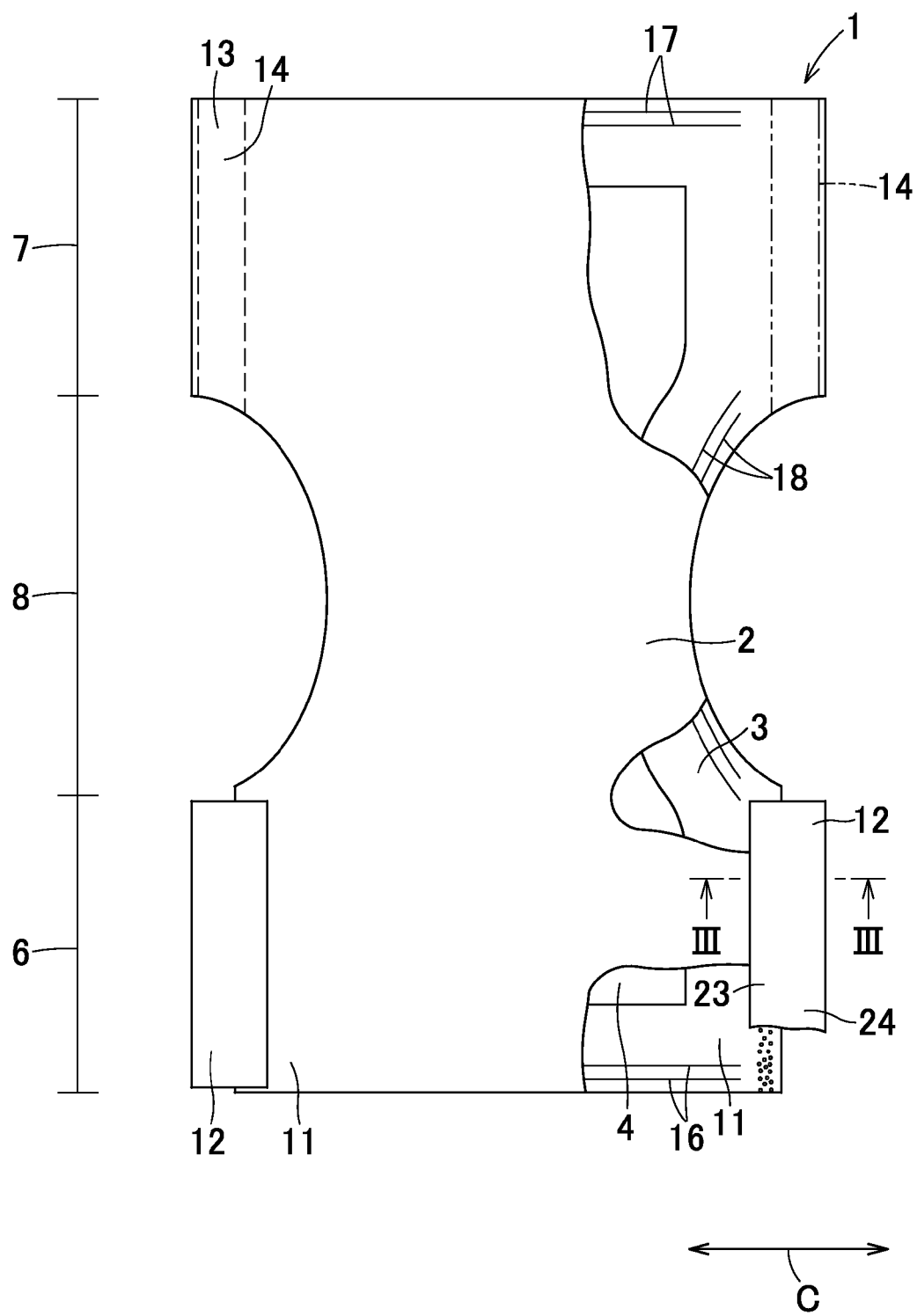
FIG. 2 is a plan view of the flatly developed wearing article (disposable diaper) as partially broken away.

FIG. 2 is a partially cutaway plan view of the flatly developed diaper 1. More specifically, in FIG. 2, the front waist region 6 and the rear waist region 7 having been connected with each other via the fastener system 20 are now detached from each other and the diaper 1 as a whole is flatly developed. Referring to FIG. 2, the core 4 has a concave shape curved inwardly and the inner and outer sheets 2, 3 sandwiching the core 4 extend outward beyond a peripheral edge of the core 4. The inner and outer sheets 2, 3 are intermittently bonded to each other outside the core 4 by hot melt adhesives (not shown). The inner and outer sheets 2, 3 are bonded also to opposite surfaces of the core 4, respectively, by hot melt adhesives (not shown). The inner and outer sheets 2, 3 sandwich there between, in addition to the core 4, waist elastic members 16 provided in the front waist region 6 so as to extend under tension in a transverse direction C, leg elastic members 17 provided in the rear waist region 7 so as to extend under tension in the transverse direction C, and the leg elastic members 18 provided in the crotch region 8 so as to extend under tension and to describe curves along peripheral edges of the respective leg-openings 32. These elastic members 16, 17, 18 are bonded to the inner sheet 2 and/or the outer sheet 3 by hot melt adhesives (not shown). It should noted here that the leg elastic members 17 and the leg elastic members 18 extend between a pair of the fixed regions 23 in the respective front lateral zones 11 but should not extend to the inner sides of the respective free regions 24. The waist elastic members 16 and the leg elastic members 18 extend between a pair of the rear fastener components 14 but should not extend to the inner sides of the respective rear fastener components 14.

Figure 3:
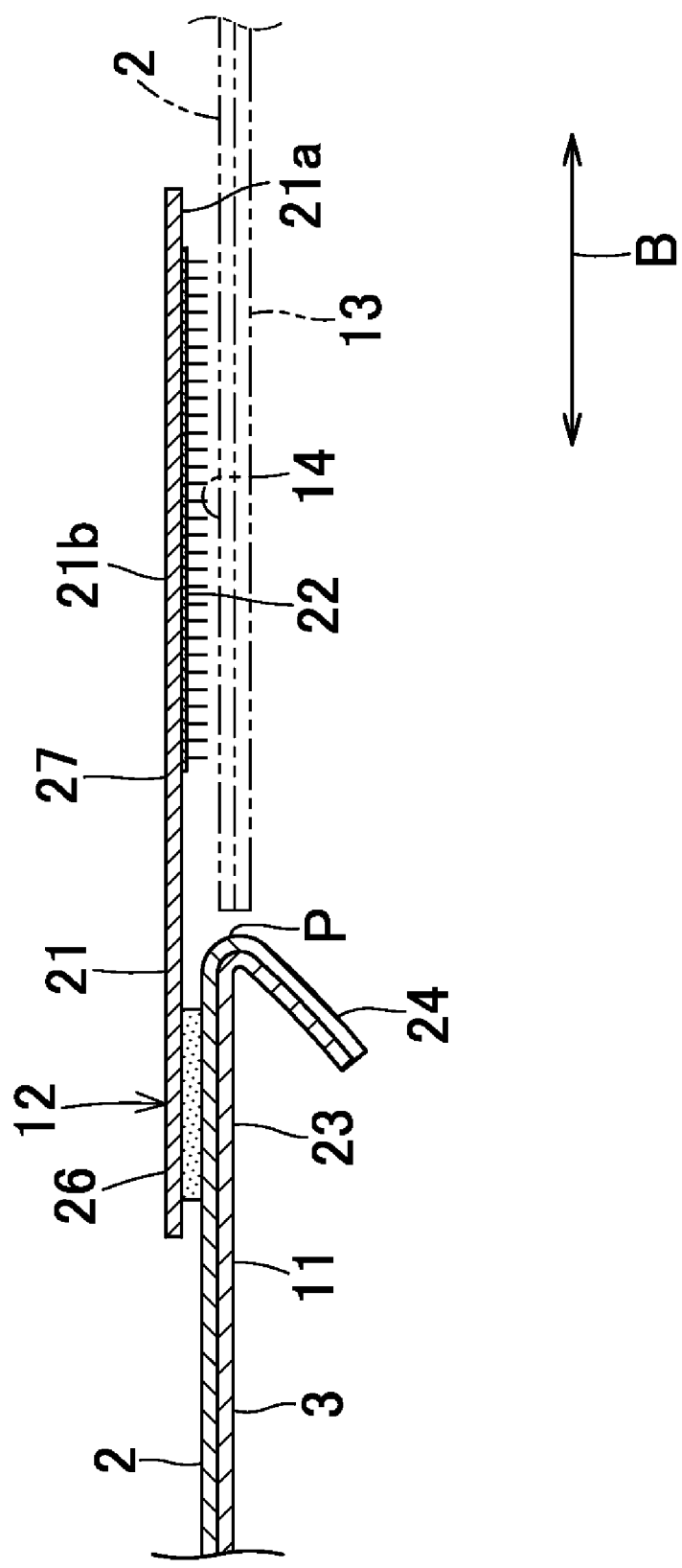
FIG. 3 is a sectional view taken along the line III-III in FIG. 2.

FIG. 3 is a sectional view taken along the line III-III in FIG. 2. The front fastener component 12 lies on the inner side of the inner sheet 2 and provided on its outer surface 21a with the hook member 22 attached thereto. The hook member 22 is adapted to come in engagement with the portion of the inner sheet 2 defining the rear fastener component 14 indicated by imaginary lines. The proximal region 26 of the base sheet strip 21 is attached to the fixed region 23 of the front lateral zone 11 by an adhesive 25.

While it is possible for the diaper 1 to take the shapes as illustrated in FIGS. 2 and 3, the diaper 1 delivered directly to the user is of the pant-shape wherein the front and rear waist regions 6, 7 previously connected to each other so that the user is able to disconnect the front and rear waist regions 6, 7 from each other and reconnect these regions to each other.

In the case of the illustrated embodiment, the hook member 22 is divided into upper and lower halves so that the base sheet strip 21 would be deformed in a space defined between these upper and lower halves and thereby would facilitate fitness of the diaper 1 to the wearer. However, division of the hook member 22 into upper and lower halves is not essential and the divided hook member 22 may be replaced by the continuous one as long as such special effect of the divided hook member 22 is not required. The rear fastener component 14 utilizing the inner sheet 2 as the loop member adapted to be engaged with the hook member 22 as the illustrated embodiment is the case may be replaced by a separately prepared loop member bonded to the inner sheet 2 as long as this separately prepared loop member is suitable for repetitive engagement/disengagement. Furthermore, the illustrated fastener system may be replaced by an alternative fastener system 20 comprising the loop member used for the front fastener component 12 and the hook member adapted to be engaged with such loop member used for the rear fastener member 14. It is also possible without departing from the scope of the invention to attach the base sheet strip 21 formed with the hook member 22 to the inner surface of the rear lateral zone 13 in the rear waist region 7 and to form the free region 24 left free with respect to the base sheet strip 21 in the rear lateral zone 13, and to engage the inner surface of the front lateral zone 11 in the front waist region 6 with the hook member 22 from the outside of the diaper 1.

Figure 4:
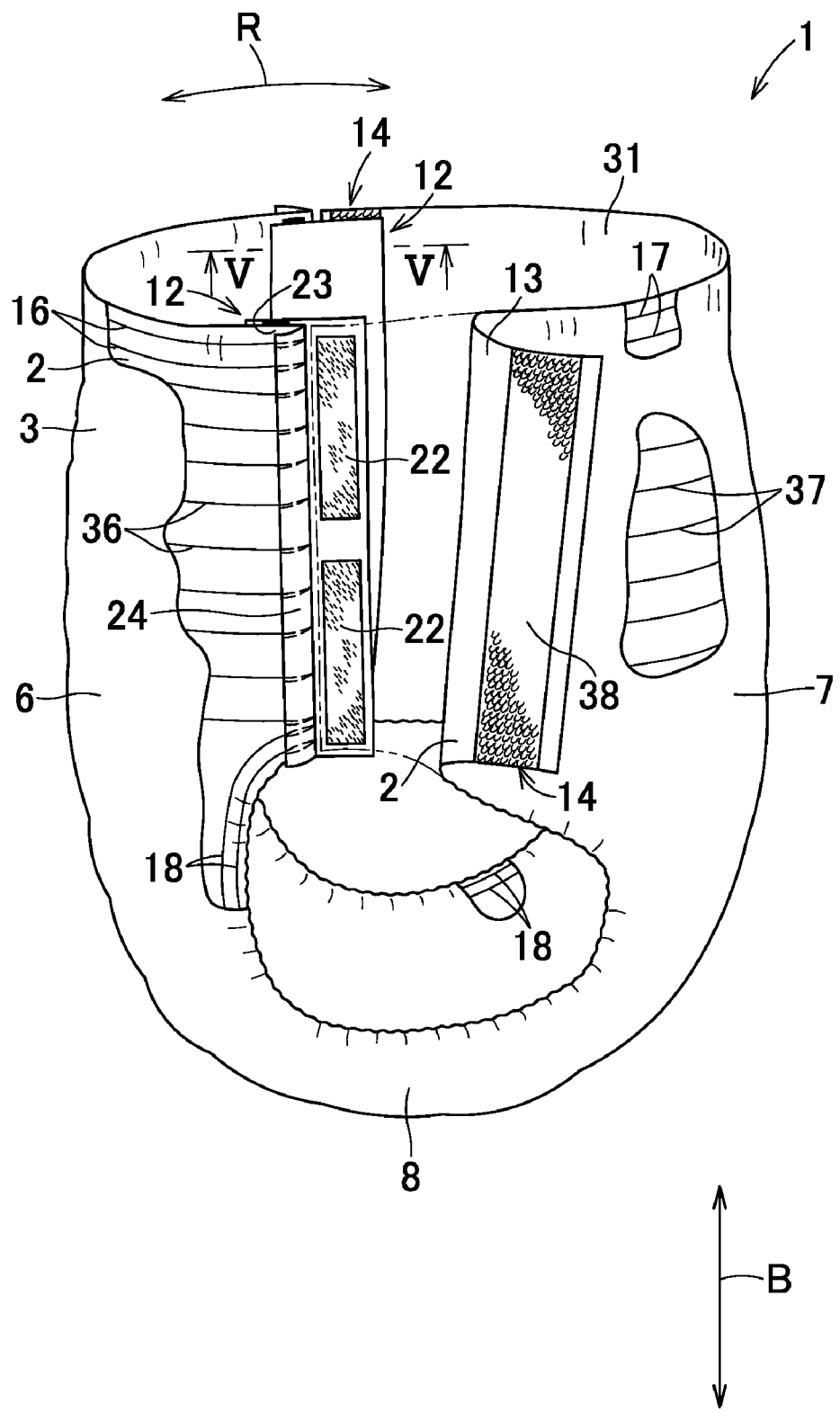
FIG. 4 is a view similar to FIG. 1, showing another embodiment.
Figure 5:
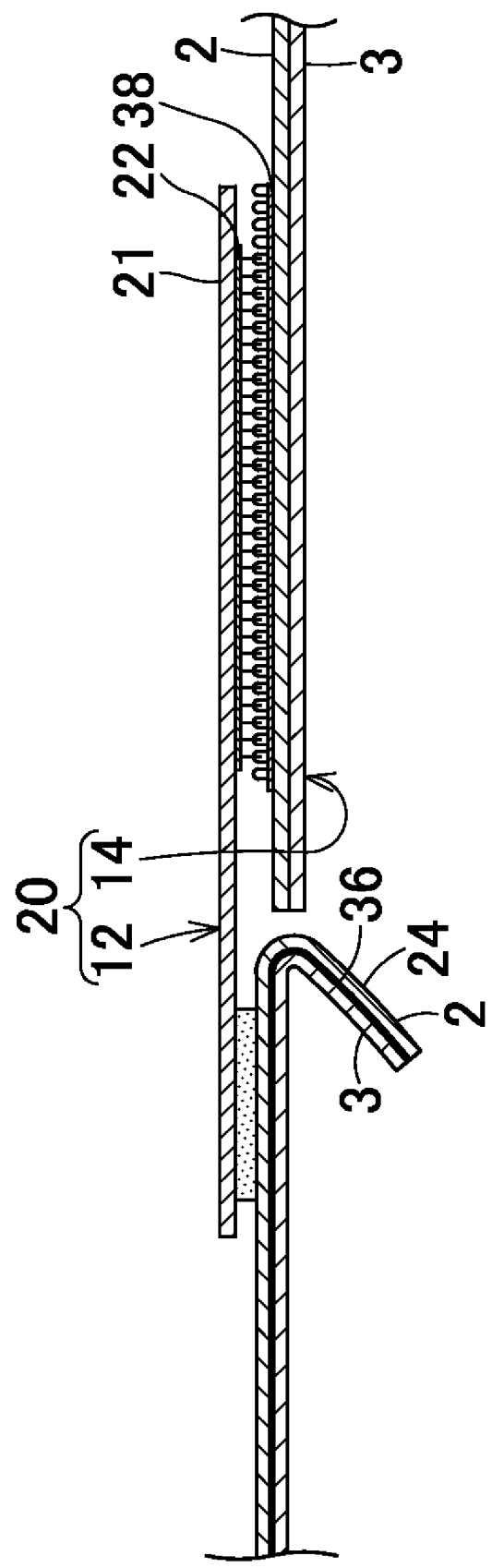
FIG. 5 is a sectional view taken along the line V-V in FIG. 4.

FIG. 4 is a view similar to FIG. 1, showing another embodiment, and FIG. 5 is a sectional view taken along the line V-V in FIG. 4. In the diaper 1 shown in FIG. 4, the front waist region 6 includes the waist elastic members 16 extending along the peripheral edge of the waist-opening 31, the leg elastic members 18 and intermediate elastic members 36 provided between the waist elastic members 16 and the leg elastic members 18 as viewed in the vertical direction B of the diaper 1 so as to extend in the waistline direction R. The line V-V in FIG. 4 is selected so that one of these elastic members 36 would be shown in a sectional view. The waist elastic members 16, the leg elastic members 18 and the intermediate elastic members 36 extend under tension to a pair of the free regions 24 of the respective front lateral zones 11 in the front waist region 6. The free region 24 is curled outward, i.e., substantially folded back in the waistline direction R with the outer sheet 3 inside as these elastic members 16, 18, 36 contract. To assist the free region 24 to be curled outward in this manner, at least the intermediate elastic members 36, more preferably, not only the intermediate elastic members 36 but also the waist elastic members 16 are bonded to the inner sheet 2 and substantially not bonded to the outer sheet 3 in the free region 24. Even when the waist elastic members 16 and the intermediate elastic members 36 are bonded to both the inner sheet 2 and the outer sheet 3, an area over which these elastic members 16, 36 are bonded to the outer sheet 3 is preferably adjusted to be smaller than an area over which these elastic members 16, 36 are bonded to the inner sheet 2. The waist elastic members 16 and the intermediate elastic members 36 bonded to the inner and outer sheets 2, 3 in this manner contract more easily in the regions bonded to the outer sheet 3 than in the regions bonded to the inner sheet 2 and thereby assure the free region 24 to be curled outward as illustrated. The rear lateral zone 13 of the rear waist region 7 is provided on the inner surface thereof with a loop member 38 prepared separately of the inner sheet 2 serving as the loop member in the embodiment shown in FIG. 1. Use of such separately prepared loop member 38 makes it possible to select the optimized loop-shape. In addition, stock materials for the inner sheet 2 can be selected on the basis of a liquid-permeability and comfort texture in disregard for its engagement with the hook member. The leg elastic members 17 and the intermediate elastic members 37 extending under tension in the waistline direction R preferably extend between a pair of loop members 38 but not to these loop members 38. With this unique arrangement of these elastic members 17, 37, regions of the respective rear lateral zones 13 in which the loop members 38 are attached define inelastic regions in which the loop members 38 are free from affection of the elastic members and none of gathers are formed.

Figure 6:
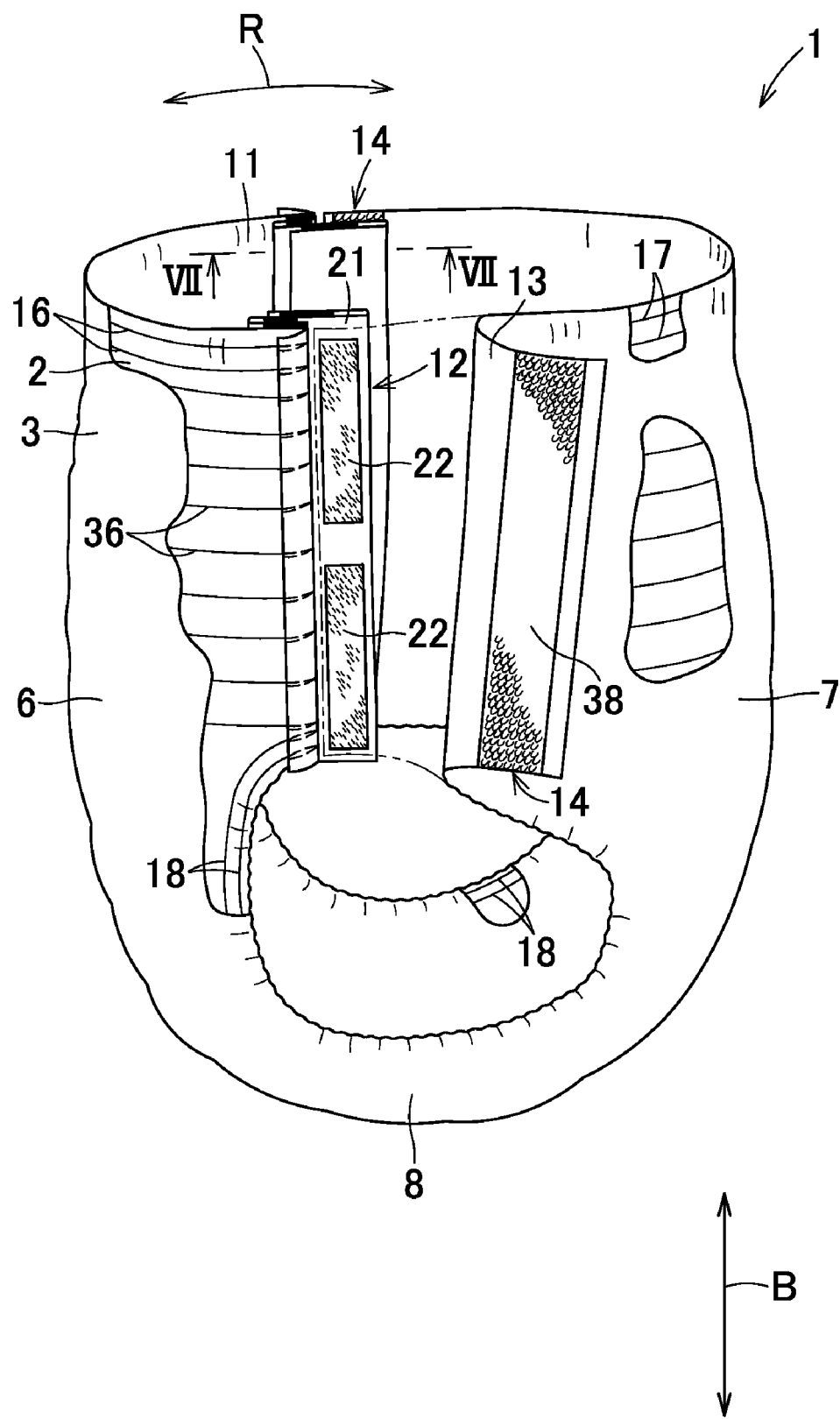
FIG. 6 is a view similar to FIG. 4, showing still another embodiment.

FIGS. 6 and 7 are views similar to FIGS. 4 and 5, showing still another embodiment of the present invention. According to this embodiment, the base sheet strip 21 for the front fastener component 12 is formed from a sheet strip 40 folded back on itself so as to have a cross section of inverted S-shape as viewed in FIG. 7. Layers defined by this sheet strip 40 folded back on itself are bonded together via first and second adhesive layers 51, 52. The sheet strip 40 is bonded also to the front lateral zone 11 of the front waist region 6 via a third adhesive layer 53. In such sheet strip 40, a region 43 defined by two layers bonded together via the first adhesive layer 51 plays the same role as the base sheet strip 21 in FIG. 3 and a region extending outward in the waistline direction R beyond the front lateral zone 11 has the hook member 22 bonded thereto. A region 44 of the sheet strip 40 integrated with the inner sheet 2 via the third adhesive layer 53 serves to improve stiffness as well as tearing strength of the front lateral zone 11 on the inner side and may be viewed as a portion of the front lateral zone 11. Therefore, the second adhesive layer 52 defines a region in which the outer surface 21a of the base sheet strip 21 in FIG. 7 is bonded to the inner surface of the front lateral zone 11 and corresponds to the adhesive 25 forming the fixed region 23 in the front lateral zone 11 in FIG. 3. It should be appreciated here that the second adhesive layer 52 serves also to prevent peel force from acting on the inner end 44a of the region 44 to peel off the third adhesive layer 53 when the region 43 of the sheet strip 40 is pulled outward in the waistline direction R. The front lateral zone 11 of the embodiment shown in FIG. 7 also includes the free region 24 defined outside the second adhesive layer 52 as viewed in the waistline direction R. The front lateral zone 11 further includes the waist elastic members 16, the leg elastic members 18 and the intermediate elastic members 36 all sandwiched between the inner and outer sheets 2, 3 and bonded under tension to at least the inner sheet 2 of the inner and outer sheets 2, 3 by hot melt adhesives (not shown). The free region 24 of the front lateral zone 11 are curved ready for being folded back in the waistline direction R as these elastic members 16, 18, 36 contract. The free region 24 is curved with the inner sheet 2, so that the side comprising the third adhesive layer 53, and the region 44 of the base sheet strip 21 face outward and the outer sheet 3 faces inward. The free region 24 curved and projecting outwardly of the diaper 1 in this manner serves to prevent the rear lateral zone 13 from needlessly beginning to get out from engagement with the front lateral zone 11.

The present invention as has been described on the basis of the disposable diaper taken as the one embodiment can be exploited in other various pant-type wearing articles such as toilet-training pants and incontinent briefs.

The invention claimed is:

1. A pant-type wearing article having a front-rear direction, a vertical direction and a waistline direction and comprising:
   a crotch region;
   a front waist region extending forward from said crotch region;
   a rear waist region extending rearward from said crotch region;
   a liquid-previous inner sheet facing the skin of a wearer of the pant-type wearing article;
   a liquid-impervious outer sheet provided beneath the liquid-pervious inner sheet;
   a pair of front lateral zones of said front waist region opposed to each other in said waistline direction and extending in said vertical direction are detachably connected to a pair of rear lateral zones of said rear waist region opposed to each other in said waistline direction and extending in said vertical direction via a pair of fastener systems so as to form a waist-opening and a pair of leg-openings and said fastener systems extend from said waist-opening to said leg-openings;
   waist elastic members extending under tension along said waist-opening, leg elastic members extending under tension along peripheral edges of said leg-openings and intermediate elastic members provided between said waist elastic members and said leg elastic members as viewed in said vertical direction and extending under tension in said waistline direction;

each of said fastener systems comprises a first fastener component on a side of said article facing the skin of a wearer and a second fastener component on a side of said article facing a garment won by the wearer and adapted to be lapped on said first fastener component from outside of said wearing article and to be repetitively engaged with and disengaged from said first fastener component and wherein said first fastener component is mounted on one of said front lateral zone and said rear lateral zone and said second fastener is mounted on other lateral zone;

said first fastener component comprises a base sheet strip attached directly to said liquid-pervious inner sheet with said liquid-impervious outer sheet on an opposite side of the liquid-previous inner sheet than the base sheet strip at one of said front and rear lateral zones and including a distal region extending outward from said one of said front and rear lateral zones in said waistline direction and an engagement region adapted to be engaged with an inner surface of said second fastener component;

said one of said front and rear lateral zones includes a fixed region in which an outer surface of said base sheet strip is partially bonded thereto and a free region lying outside said fixed region as viewed in said waistline direction so as to be left free with respect to said base sheet strip; and said free region normally takes a posture folded back configuration in said waistline direction so that an outer surface of said one of said front and rear lateral zones lie inside the folded back configuration, wherein said free region includes at least said waist elastic members and said intermediate elastic members and is kept in said posture folded back in said waistline direction under contraction of said waist elastic members and said intermediate elastic members in said waistline direction.

2. The wearing article defined by claim 1, wherein said free region takes a posture folded back in said waistline direction along a folding line extending in said vertical direction.

3. The wearing article defined by claim 1, wherein said free region takes a posture folded back in said waistline direction along a folding line extending in said vertical direction.

* * * * *